United States Patent [19]

Daikuzono

[11] Patent Number: 5,342,358
[45] Date of Patent: Aug. 30, 1994

[54] APPARATUS FOR OPERATION BY LASER ENERGY

[75] Inventor: Norio Daikuzono, Ichihara, Japan

[73] Assignee: S.L.T. Japan Co., Ltd., Tokyo, Japan

[21] Appl. No.: 2,769

[22] Filed: Jan. 12, 1993

[51] Int. Cl.$^5$ ............................................... A61B 17/36
[52] U.S. Cl. ........................................ 606/45; 606/28; 606/15; 606/16
[58] Field of Search .................... 606/2, 3, 13–16, 606/27–31, 45, 46, 49

[56] References Cited

U.S. PATENT DOCUMENTS

| | | | |
|---|---|---|---|
| 3,865,113 | 2/1975 | Sharon | 128/395 X |
| 4,116,198 | 9/1978 | Roos | 606/46 |
| 4,249,533 | 2/1981 | Komiya | 606/15 |
| 4,736,743 | 4/1988 | Daikuzono . | |
| 4,834,095 | 5/1989 | Miller | 606/45 |
| 4,994,060 | 2/1991 | Rink et al. | 606/28 |
| 5,071,222 | 12/1991 | Laakmann et al. | 606/28 X |
| 5,078,712 | 1/1992 | Easley et al. | 606/16 |
| 5,151,097 | 9/1992 | Daikuzono | 606/16 |

FOREIGN PATENT DOCUMENTS

| | | | |
|---|---|---|---|
| 70459 | 1/1983 | European Pat. Off. | 606/16 |
| WO 06641 | 4/1992 | European Pat. Off. | 606/16 |

*Primary Examiner*—Peter A. Aschenbrenner
*Attorney, Agent, or Firm*—Lowe, Price, LeBlanc & Becker

[57] ABSTRACT

An apparatus performs operations such as incision, coagulation and evaporation of the tissue of a living body such as human body with laser lights. An apparatus for performing a surgical operation of the tissue of a living body with laser lights while contacting a blade with the tissue of the living body comprising a holding portion which is held by an operator, a blade which is integral with the holding portion and is made of a material which generates heat on exposure to laser lights and can not transmit the laser lights therethrough, and an optical fiber which receives laser lights for emitting the laser lights from the front end thereof, said blade being positioned in such a manner that a part of said blade is located in the irradiation area of the laser lights from said optical fiber and said optical fiber being movable toward and away from said blade while said optical fiber is held by said holding portion.

14 Claims, 10 Drawing Sheets

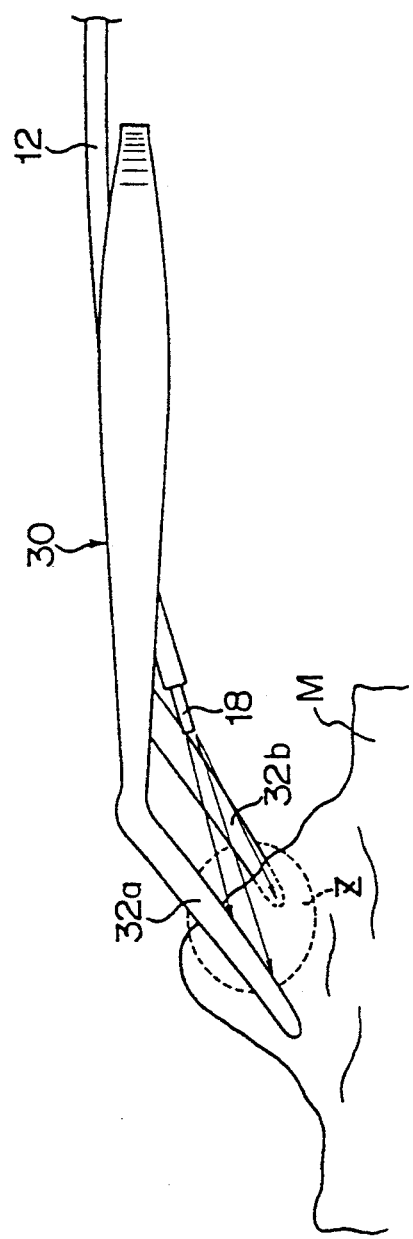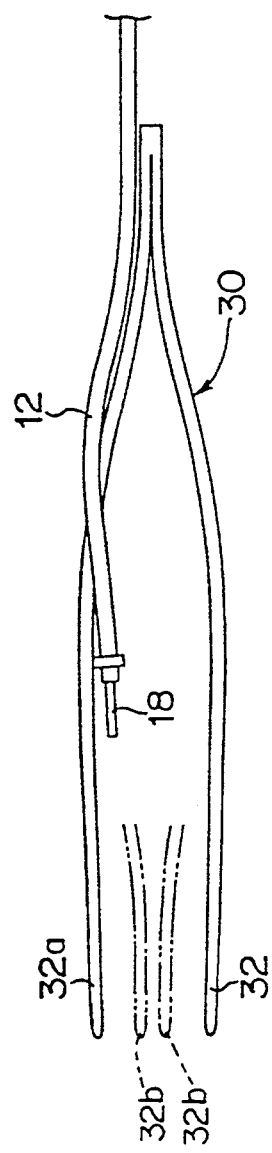

APPARATUS FOR OPERATION BY LASER ENERGY

DETAILED DESCRIPTION OF THE INVENTION

Field of the Invention

The present invention relates to an apparatus for performing operations such as incision, coagulation and vaporization of the tissue of a living body such as human body by using laser lights. The apparatus can be also used for internal treatment using an endoscope as well as surgical operation.

Recently, surgical operations or internal operations for incision, coagulation and vaporization of the tissue of a human body have been often conducted by using laser energy. Operation with laser lights has an advantage over operations with a mechanical knife in that bleeding is less. Operation of an organ in the vicinity of the heart with laser lights has an advantage over operations with an electric knife in that shock to the heart is less. The term "laser lights", as used herein, is intended to comprehend laser energy fluxes as available from conventional laser energy sources. Further it has an great advantage in that the curing speed of the operated tissue is fast.

Traditional laser knives typically have been of a non-contact type. The present inventor has proposed a contact type laser knife which makes it easy to perform an operation by bringing a contact probe into the tissue in U.S. Pat. 4,736,743. The laser knife has a contact chip or a contact probe at the front end of an optical fiber. Laser lights are emitted from the front end of the optical fiber and are transmitted through the contact probe and are emitted from the front end of the contact probe.

Since the contact probe is made of sapphire or quartz, it is easily broken or damaged if an excessive external force is erroneously applied thereto or it is brought into contact with the other instruments in an operation room. In this case, it is necessary to exchange the damaged contact probe with a new contact probe and to mount the new contact probe on a holder. If there is not enough time, it is necessary to exchange the older holder having a spare holder with a new contact probe.

In any case, damages to the contact probe during emergent operation should be avoided.

Since it takes an extended period of time to fabricate the contact probe into a given configuration depending upon the use, the manufacturing cost becomes higher, and the material per se is expensive.

Since the contact probe for incision is fabricated into a configuration which is exclusively used therefor, it is necessary to exchange the contact probe for incision with a contact probe for coagulation or vaporization if coagulation or vaporization of the peripheral tissue is wanted to be performed.

SUMMARY OF THE INVENTION

It is therefore an object of the present invention to provide an apparatus for performing an operation with laser lights, which has a high durability and is economical.

It is another object of the present invention to provide an apparatus for performing an operation with laser lights, which may be used for incision, coagulation and vaporization.

The above mentioned objects are accomplished by providing an apparatus for performing a surgical operation of the tissue of a living body with laser lights while contacting a blade with the tissue of the living body comprising a holding portion which is held by an operator, a blade which is integral with the holding portion and is made of a material which generates heat on exposure to laser lights and can not transmit the laser lights therethrough, and an optical fiber which receives laser lights for emitting the laser lights from the front end thereof, said blade being positioned in such a manner that a part of said blade is located in the irradiation area of the laser lights from said optical fiber and said optical fiber being movable toward and away from said blade while said optical fiber is held by said holding portion.

The blade is made of a non-exothermic metallic material which will not generate heat on exposure to laser lights as well as exothermic metallic material which generates heat on exposure to laser lights. In any case, the metallic material may be coated on the surface thereof with an exothermic material which generates heat on exposure to laser lights. In other words, if a non-exothermic material is used, inherent ability for incision is exhibited. If an exothermic material is used, the exothermic degree is advantageously enhanced. However, a material which will not be melt on exposure to laser lights is selected for the blade.

The material which forms the blade is preferably selected from the group of stainless steel, titanium, tantalum and nichrome. The exothermic material is one which is selected from the group of graphite, ion oxides and magnesium oxides and the mixture thereof. A coating layer of the exothermic material may be formed by depositing the exothermic material on the surface of a main body of the blade while the blade surface is melt at high temperature, or by applying the exothermic material on the surface of the blade main body after preliminarily dispersing the exothermic material in a heat resistant bonding material.

The holding portion is made of a metallic pipe. The blade is held on the metallic pipe without any interposing adiabatic member therebetween. The metallic pipe has a length of 10 cm or more. The heat which is generated when the blade is irradiated with laser lights is conducted to the metallic pipe so that the heat is diverged into air.

A guide pipe is held on the holding portion and optical fiber is provided so that they are movable forward and rearward within and along the guide pipe and the position of the optical fiber in a longitudinal direction within the guide pipe can be fixed.

In the present invention, the optical fiber is movable toward and away from the blade.

In this case, the optical fiber is designed so that the irradiation area of the laser lights from the front end of the optical fiber has a projection area which is larger than that of the blade upon the tissue of a living body. Coagulation or vaporization of the tissue can be made by directly irradiating the tissue with laser lights from the front end of the optical fiber while the optical fiber is remote from the blade. Incision can be made by using the energy possessed by the laser lights as an exothermic energy of the blade by approaching the optical fiber to the blade for converging the laser lights from the front end of the optical fiber on the blade. Therefore two mode operations such as incision and coagulation or vaporization is possible with a single instrument.

The blade is formed in such a manner that it is bent in on direction at the front end thereof, the bent portion of the blade will contact with the tissue of the living body on the front side thereof and is irradiated with laser lights on the rear side of said bent portion. The blade may be used for cauterization of a projected tumor, for example.

The blade may be open-looped in such a manner that it extends forward from the holding portions, the base ends of the blade being held by respective holding portions, irradiation area of the laser light from the front end of the optical fiber is preset toward the front end of the loop.

The loop may be slanted at the front end thereof so that the irradiation axis of the laser lights intersects with a plane on which the front end portion of the loop is placed.

The holding portions may be in the form of scissors and an optical fiber is held on said holding portion so that the laser lights are incident upon the blade edge of the scissor.

The holding portions may be in the form of scissors and two bundle of optical fibers are held by said holding portions so that the laser lights are incident upon the respective blade edge. This apparatus may be effectively used for incision of the tissue.

The holding portions may be in the form of tweezers and optical fibers may be held on said holding portions so that the laser lights are incident upon the pressure contact surface of each of the front end of the holding portion. This apparatus is capable of performing an operation such as coagulation while the tissue is tweezed and picked up.

A radio frequency oscillator may be connected to the blade so that the blade can be used as an electric knife.

BRIEF DESCRIPTION OF THE DRAWINGS

FIG. 11 is a perspective view showing a further embodiment of tweezers like apparatus;

FIG. 12 is a plan view showing the apparatus of FIG. 11;

DESCRIPTION OF THE PREFERRED EMBODIMENTS

Figure 1:
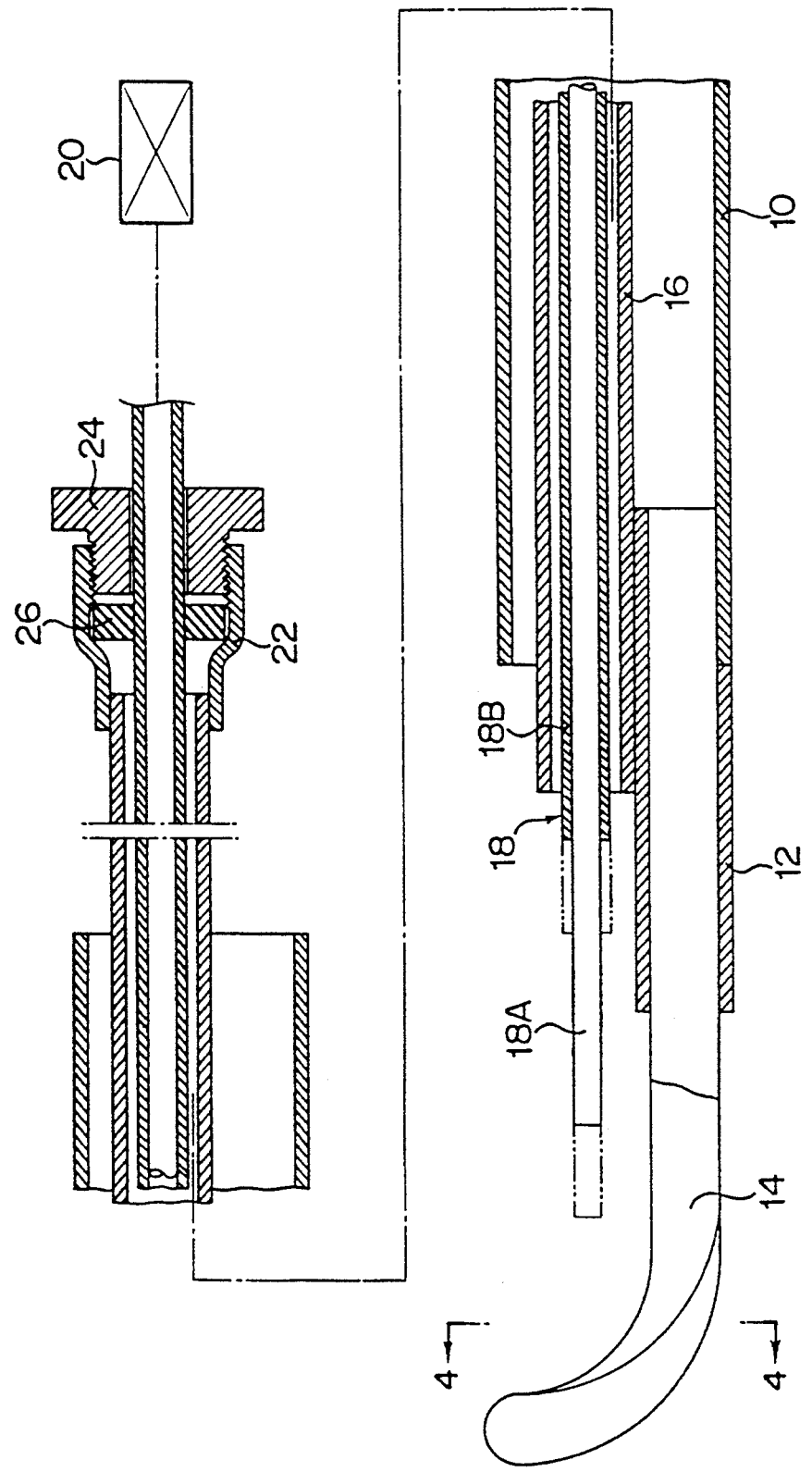
FIG. 1 is a longitudinal sectional view showing an embodiment of an apparatus of the present invention.

The present invention will become more apparent from the description of preferred embodiments shown in the drawings.

Figure 2:
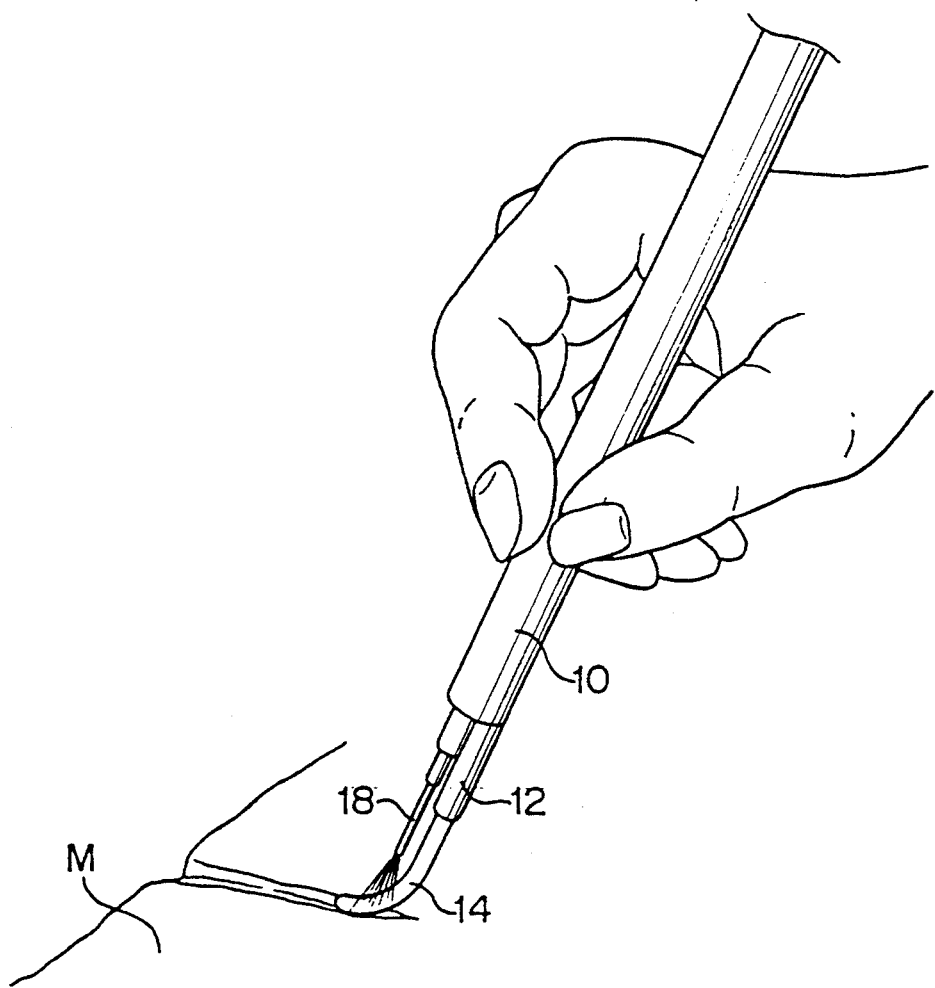
FIG. 2 is a perspective view showing an application of the apparatus.
Figure 4:
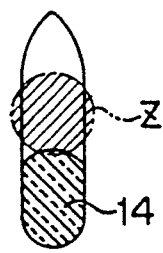
FIG. 4 is an explanatory view showing the irradiation area of laser lights when an optical fiber is moved toward a blade.
Figure 5:
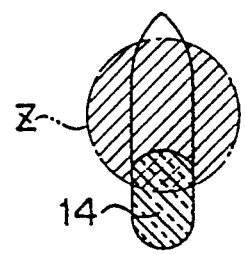
FIG. 5 is an explanatory view showing the irradiation area of a laser light when the optical fiber is remote from the blade.

FIGS. 1 and 2 show a first embodiment of an apparatus of the present invention. A reference numeral 10 denotes a holder pipe which is held by an operator and is made of a stainless pipe for example. A mounting pipe 12 is integrally secured to the front end of the holder tube 10 by means such as welding. A J-shaped hook blade 14 is integrally secured to the mounting pipe 12 by means such as welding. The hook blade 14 is circular in cross-section along the length thereof from the base end to an intermediate position and is flat in cross-section from along the length the position to the front end and is sharp on the front side (left side as viewed in FIG. 1) as shown in FIGS. 4 and 5. A guide pipe 16 is provided within the holder pipe 10. The guide pipe 16 is integrally secured to the above-mentioned pipe 12 by means such as welding so that it is also integral with the holder pipe 10.

Optical fiber 18 are inserted in the guide pipe 16 in spaced manner therewith. The optical fiber 18 is optically coupled to a laser generator 20 so that it transmits the laser lights from the laser generator 20 for emitting the laser lights from the front end of the fiber 18. A sleeve 22 is mounted on the base end of the guide pipe 16 as means for positioning the optical fiber 18. A pressure contact member 26 which is made of rubber, for example, is compressed by leftward movement as viewed in FIG. 1 of a plug 24 which is threadably fitted into the sleeve 22. Compression of the pressure contact member 26 causes the member 26 to pressure contact with the outer periphery of the optical fiber 18 so that the optical fiber 18 is firmly secured to the guide pipe 16. The optical fiber 18 can be freely moved by drawing the optical fiber 18 rightward or forcing the fiber leftward while the holder pipe 10 is held with a left hand after compression of the pressure contact member 26 is released by rotating the plug 26 in an opposite direction. If the optical fiber 18 is forced leftward, it is moved toward the hook blade 14 as represented by a phantom line in FIG. 1 and is moved away from the hook blade 14 if it is withdrawn. The illustrated optical fiber 18 has a main body 18A which is coated with a protection tube 18B.

Laser lights are emitted from the front end of the optical fiber 18 in such a manner that they diverge at a small divergence angle. When the optical fiber 18 is moved toward the hook blade 14 as shown by the phantom line of FIG. 1, the irradiation area Z with the laser lights has a width equal to that of the hook blade 14 so that the laser lights are incident upon the rear side of the hook blade 14. In contrast to this, when the optical fiber 18 is moved remote from the hook blade 14 the width of the irradiator area Z becomes larger than that of the hook blade 14 as shown in FIG. 5. Accordingly, although some of the laser lights are incident upon the rear side of the hook blade 14, the other laser lights are directly incident upon the tissue.

Such an apparatus can be used for incision as shown in FIG. 2. Irradiation with laser lights is conducted while the holder pipe 10 is held with a hand and the front side of the hook blade 14 is abutted upon the tissue M. The laser light are incident upon the rear side of the hook blade 14 and the light incident area intensively generates heat. The heat is transmitted to the front side of the hook blade 14 so that the cauterization of the tissue is performed with this heat. In this process, incision can be made by moving the hook blade 14 in one direction as shown in the drawing.

In this case, prior to incision the tissue around an object to be incised can be coagulated by moving the hook optical fiber 18 from the hook blade 14. This method exhibits hemostatic capability by coagulation of the tissue.

Figure 3:
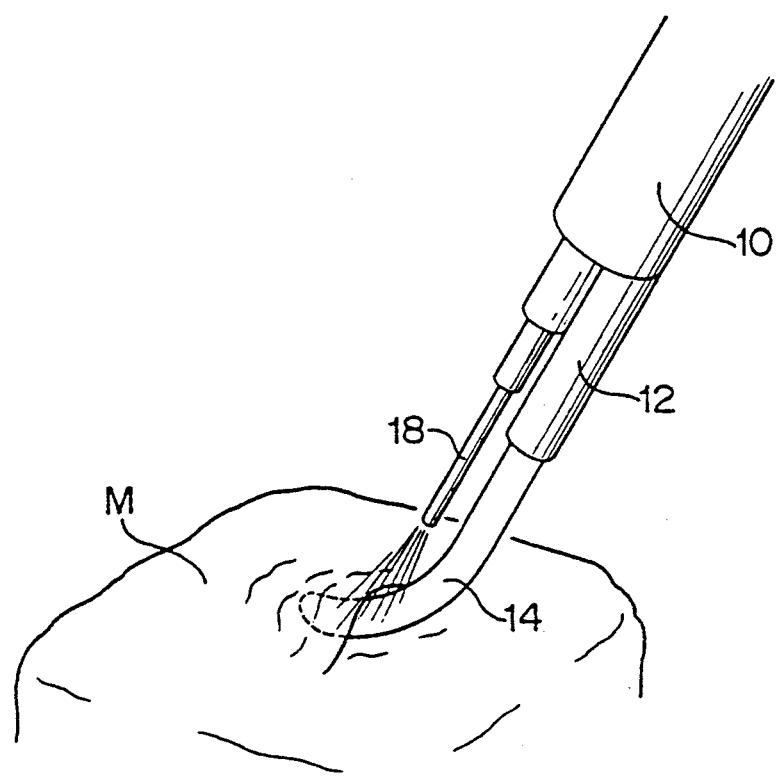
FIG. 3 is a perspective view showing another application thereof.

The apparatus having the hook blade 14 is applicable in a manner shown in FIG. 3. While a part of the tissue for example veins or muscle is hooked up on the rear side of the hook blade 14 at the front end thereof, the hooked up tissue is irradiated with the laser lights. In this case, the hooked up tissue per se is directly irradiated with laser lights and after the laser lights have transmitted through the tissue, the laser lights are incident upon the hook blade 14. The hook blade 14 is heated and incision is also conducted with the heat from the blade 14.

If the front end of the optical fiber 18 is damaged due to contact of the front end of the optical fiber 18 with the tissue and the like, the optical fiber 18 can be reused by advancing the optical fiber by the length of the damaged fiber. If necessary, the damaged optical fiber 18 may be replaced with a new optical fiber. Since the optical fiber 18 is a universal article, it is very economical in comparison with the above mentioned contact probe or contact chip. The cost of the whole apparatus is economical.

Figure 6:
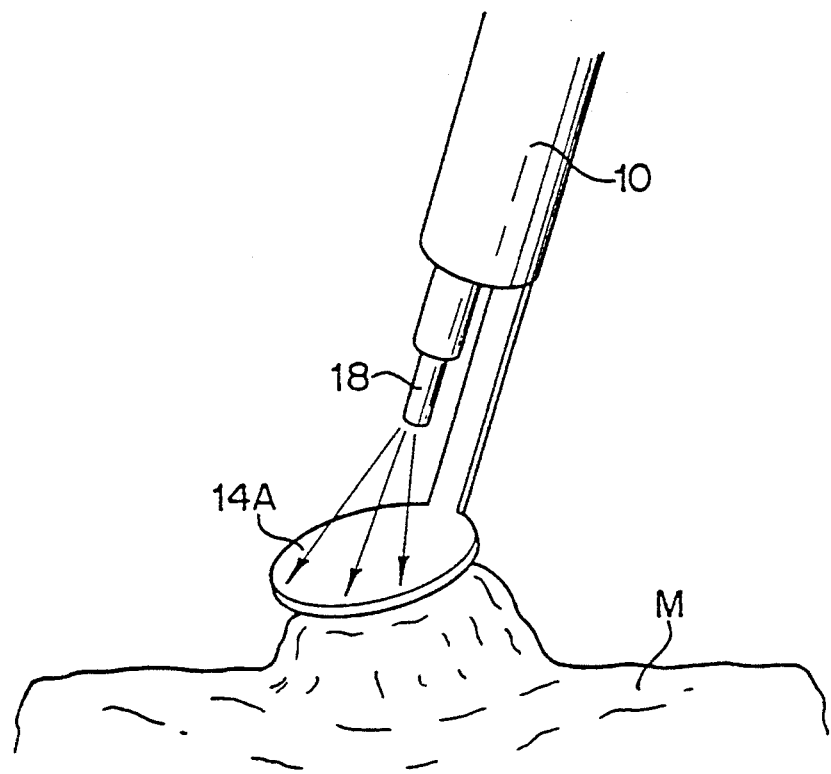
FIG. 6 is a perspective view showing another embodiment of an apparatus.

FIG. 6 shows the structure of a second apparatus. The apparatus has a flat plate like blade 14A in lieu of the hook blade 14 at the front end thereof. The preferred utilization of the blade 14 is to cauterize the tumors or soared tissue by applying the front side of the flat plate like blade 14A thereon and irradiating the rear side of the blade 14 with laser lights.

Figure 7:
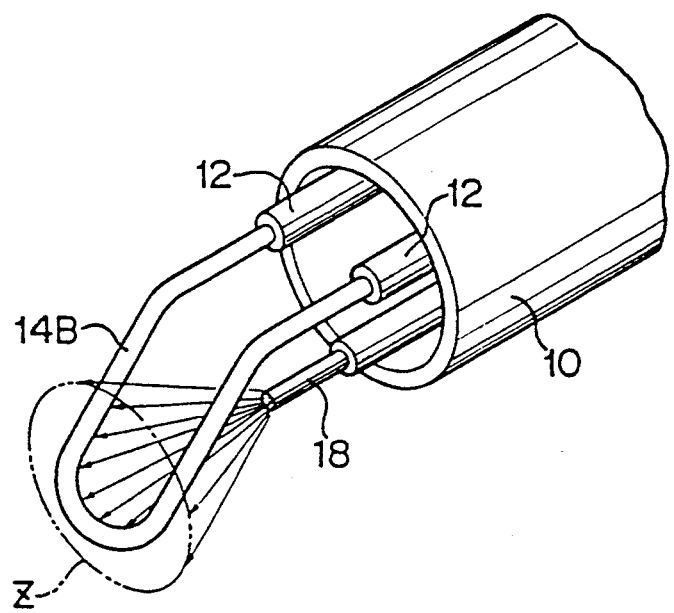
FIG. 7 is a perspective view showing an apparatus having an open looped blade.
Figure 8:
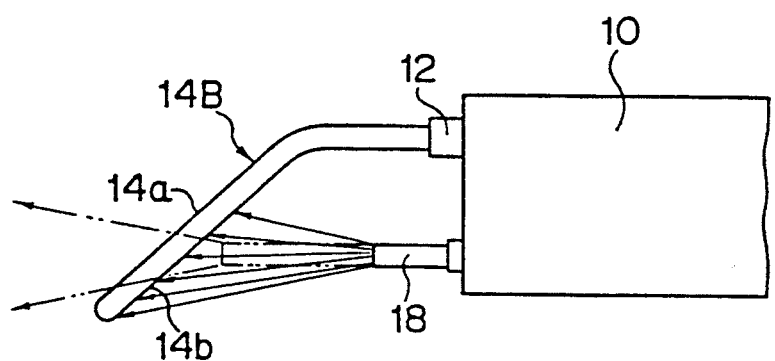
FIG. 8 is an elevational view of the apparatus of FIG. 7.

FIGS. 7 to 10 shows an embodiment of an apparatus having an open-looped blade. The looped blade 14A shown in FIGS. 7 and 8 is secured relative to the holder pipe 10 so that it is secured to the mounting pipes 12 at the open ends thereof and extends forward in a parallel relationship and obliquely slanted downward at the front end thereof.

The optical fiber 18 is positioned in such a manner that the front end of the looped blade 14B is located in the irradiation area Z of the laser lights Z. The looped blade 14B in this embodiment can adopt various operations such as wide incision by pulling the holder pipe 10 rearward while the front end of the loop is pressed upon the object tissue, removing of a projected tissue by moving the holder pipe 10 on a plane while applying the whole of the front side 14a upon the tissue, and removing of a projected tissue and vaporazation of the tissue by positioning the projected tissue between the rear side 14b and the front end of the optical fiber 18.

Figure 9:
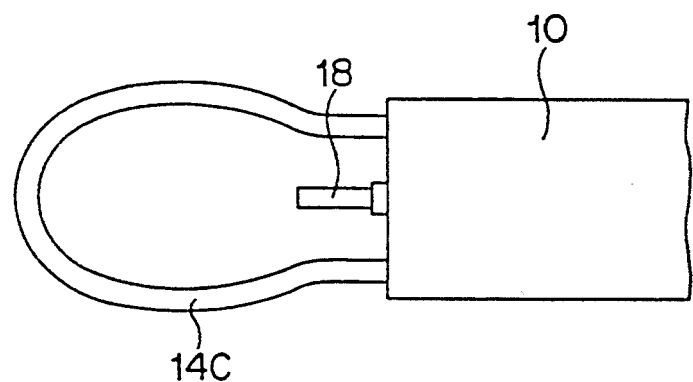
FIG. 9 is a plan view showing a further embodiment which is different from the foregoing embodiment in shape thereof.
Figure 10:
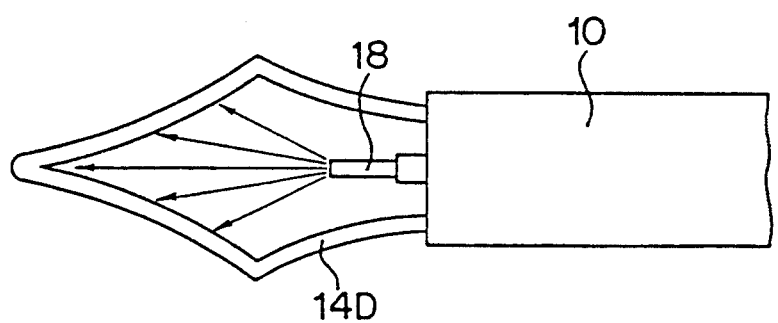
FIG. 10 is a plan view showing a further embodiment.

FIG. 9 shows an embodiment in which the whole looped blade 14C is on the same plane. FIG. 10 shows an embodiment of a looped blade 4D having a substantially rhombi shape which is common to the electric surgical knifes.

FIGS. 11 and 12 show an embodiment in which a tweezers-shaped holder is integral with a blade. A tweezers-like holder 30 is integrally provided with pressure contact blades 32a, 32b at the front end thereof. A guide pipe 12 is mounted on the holder 30 so that it extends along one side of the holder 30. The optical fiber 18 1s movable forward and rearward within the guide pipe 12. In this ease, the optical fiber 18 is designed in such a manner that the pressure contact portions 32a, 32b are also irradiated with laser lights when the tissue is tweezed between the pressure contact portion 32a, 32b.

Such an apparatus like tweezers can be used for irradiation of the tissue M at an object position with laser lights while it is tweezed and lifted up with pressure contact portions 32a, 32b as shown in FIG. 11.

Figure 13:
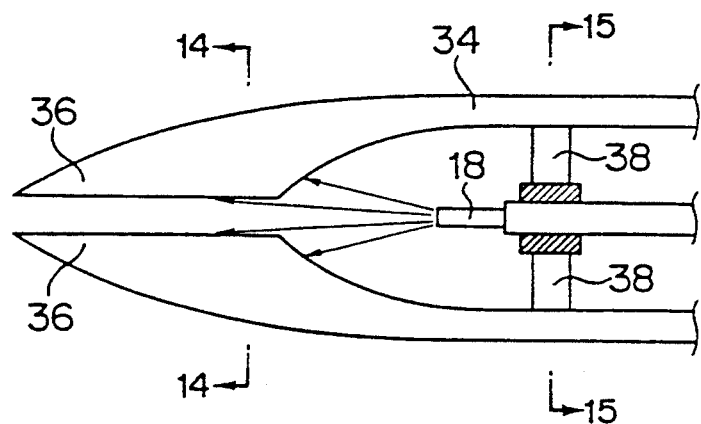
FIG. 13 is a front view showing a scissors type apparatus.
Figure 14:
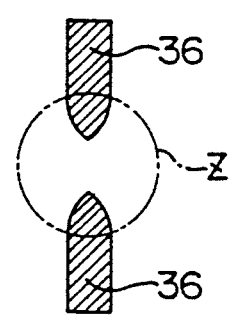
FIG. 14 is a sectional view taken along the line 14—14 in FIG. 13.
Figure 15:
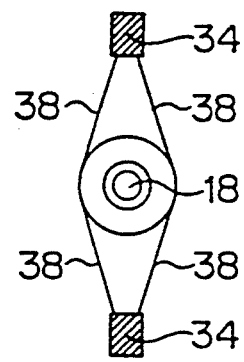
FIG. 15 is a sectional view taken along the like 15—15 in FIG. 13.

FIGS. 13 to 15 show an embodiment in which a scissors like holder is integral with an incision blades. A tweezers-like holders 34 are integrally provided with incision blade 36 at the front end thereof. A guide pipe 12 is held between holders 34 so that left spring members 38 are disposed between each of the holders 34 and the guide pipe 12. Optical fiber 18 is movable forward and rearward with the guide pipe 12. The optical fiber 19 are positioned so that they emit laser lights toward the edge of the incision blades 36.

This apparatus conducts incision of the tissue by emitting laser lights from the front end of the optical fiber 18 while tweezing the tissue between the incision blades 36. In this case, when the incision blades 36 are moved toward each other, the leaf springs 38 will flex. Release of tweezing of the tissue returns the guide pipe 12 and the optical fiber 18 to a home center position.

Figure 16:
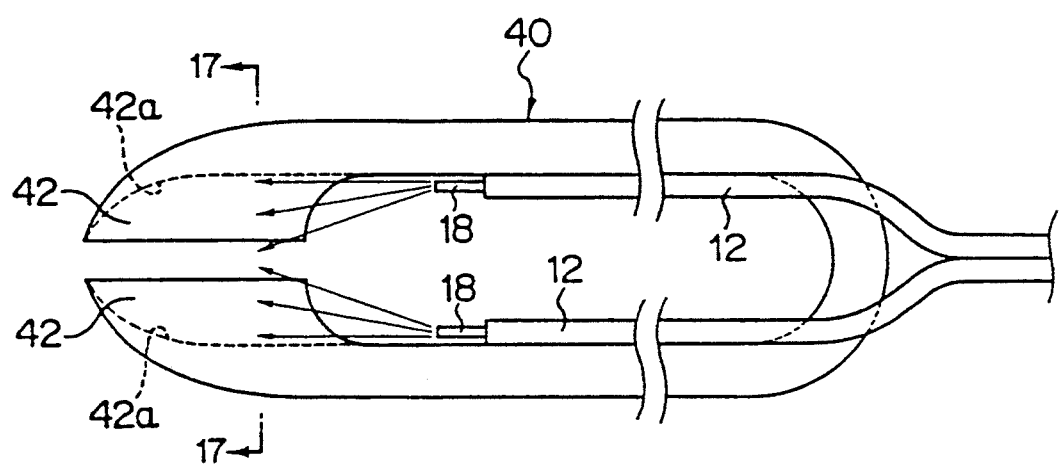
FIG. 16 if a front view showing another scissors type apparatus.
Figure 17:
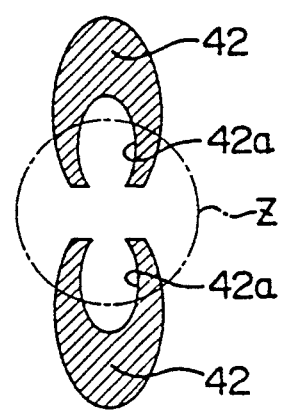
FIG. 17 is a sectional view taken along the line 17—17.
Figure 18:
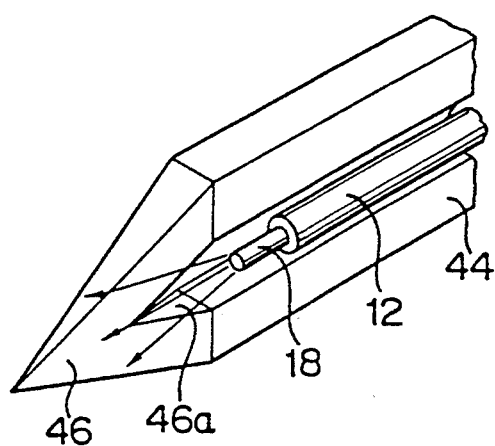
FIG. 18 is a perspective view showing a piercing apparatus.

Although the incision blades 36 are irradiated with laser lights emitted from a optical fiber, an optical fiber 18 may be mounted on each of the holders 40 so that it emits laser lights toward each of the biasing blades 42 of the tweezers-like holder 40 as shown in FIGS. 16 and 17. Each of the illustrated blade 42 is formed with a recess 42a.

This apparatus is mainly preferable for hemostasis by tweezing veins between the biasing blades 42.

Figure 19:
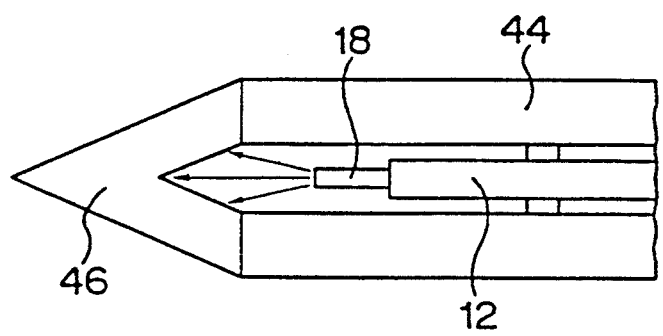
FIG. 19 is an elevational view of the apparatus of FIG. 18.

An embodiment shown in FIGS. 19 and 19 is effective for mainly piercing. A sharp pyramid shaped piercing blade 46 is integral with the front end of a thin plate-like holder 44. A guide pipe 12 and optical fiber 18 are secured in a space within the holder 44. The piercing blade 46 is formed with a notch window 46a so that the laser light are directly incident upon the tissue via the window when the optical fiber 18 is retracted.

This apparatus can be used for piercing the tissue by irradiating the rear side of the piercing blade 46 with laser light by pressing the front end of the piercing blade 46 into the tissue.

At least the above mentioned blade in the present invention is made of a material which can not transmit the laser lights. The typical material is a metal which may be selected from the group of stainless steel, titanium, tantalum, nichrome and the like. If the blade is electrically conductive, the blade which is connected with a radio frequency oscillator may be used as a surgical electric knife. In use of the electric knife, an opposite polar plate for the blade is preliminarily attached to a patient.

If the blade of the present invention is used as an electrical knife terminal in such a manner, incision of the tissue can be made without laser light irradiation. In the course of the incision, the laser lights can be radiated from the front end of the optical fiber when vaporization and/or coagulation of the tissue is necessary. Incision speed or incision capability can be enhanced by radiating the laser lights while applying radio frequency waves to the blade.

Use of the apparatus with the electric knife will be further described. If the apparatus is used as an electric knife, the incision ability is generally higher than the case in which laser lights are used. However, the electric knife has little hemostatic capability in comparison with the case in which laser lights are also used and has a coagulation ability which is not so high and gives large damages to the tissue. Therefore, the blade is used as an electric knife for making an incision operation at a high incision ability and it is preferable that the tissue be irradiated with laser lights for enhancing the hemostatic ability in the course of the incision operation or if the tissue is bleedable coagulation ability can be enhanced and an increase in damage to the tissue can be prevented by irradiating the tissue with laser lights while the electric knife is used in a coagulation mode. Use of an electric knife with irradiation of the tissue with laser lights provides distinct advantages which have not been found in the prior art.

Although it is not essential to coat a blade with an exothermic material, the exothermic efficiency is enhanced if a coating layer of the exothermic material is formed. Examples of the exothermic material may be one which is selected from the group of carbon, graphite, iron oxides, magnesium oxides or the mixture thereof.

The blade of the present invention may be attached to an endoscope. In this case, the above mentioned apparatus may be inserted into an introducing bore of the endoscope or may be in such manner that a blade is mounted on the front end of an insertion sheath or catheter and an optical fiber or a guide pipe is inserted into the sheath or disposed within the sheath.

The apparatus may be mounted on a Zelektscope. If the blade is mounted on the sheath or the catheter for internal treatment, these component constitute "a holding portion" used herein. It is preferable that the holder or guide pipe be flexible for internal treatment.

What is claimed is:

1. An apparatus for performing a laser-energy powered surgical operation on the tissue of a living body while contacting a blade with the tissue, comprising:
   a holding portion to be held by an operator;
   a blade which is integral with the holding portion, the blade being made of a material which generates heat on exposure to laser energy emitted at the blade and which does not transmit the laser energy therethrough; and
   an optical fiber held by the holding portion for emitting laser energy from a front end surface to the blade,
   wherein said blade is positioned in such a manner that a part thereof is located in an area irradiated by the laser energy emitted from said optical fiber, and wherein said optical fiber is held so that the laser energy emitting front end surface thereof is movable toward and away from said blade while said optical fiber is held by said holding portion.

2. The apparatus according to claim 1, wherein:
   a main body of the blade is made of a metallic material which does not melt on exposure to the emitted laser energy and is coated on an outer surface with an exothermic material which generates heat on exposure to the emitted laser energy.

3. The apparatus according to claim 1, wherein:
   the material of the main body of the blade is selected from a group of materials consisting of stainless steel, titanium, tantalum and nichrome.

4. The apparatus according to claim 1, wherein:
   said exothermic material comprises a material selected from a group of materials consisting of carbon, graphite, iron oxide and magnesium oxide or a mixture thereof.

5. The apparatus according to claim 1, wherein:
   said holding portion is made of a metallic pipe, said blade being held to the metallic pipe without any interposing adiabatic member therebetween, said metallic pipe having a length of at least 10 cm.

6. The apparatus according to claim 1 further comprising:
   a guide pipe held on the holding portion, the optical fiber being provided to be movable forward and rearward within and along the guide pipe so that the position of the optical fiber in a longitudinal direction within the guide pipe can be selectively fixed relative thereto.

7. The apparatus according to claim 1, wherein:
   said optical fiber is formed so that the irradiation area of the laser lights from the laser energy emitting front end of the optical fiber irradiates a projection area which is larger than an area of the blade on the tissue being operated on by the blade.

8. The apparatus according to claim 1, wherein:
   the blade is formed to be bent in a first direction at a distal portion thereof, so that the bent portion of the blade will contact with the tissue of the living body on a front side and is irradiated with the emitted laser energy on a rear side of said bent portion.

9. The apparatus according to claim 1, wherein:
   said blade has an open-looped distal end portion and extends forwardly from the holding portion with a base end of the blade being held by the holding portion, an irradiation area of the laser energy emitted from the front end surface of the optical fiber being located at a front end portion of the blade.

10. The apparatus according to claim 9, wherein:
    the open-looped portion is slanted at a front end thereof so that an irradiation axis of the laser energy emitted thereon intersects with a plane on which the front end portion of the loop is placed.

11. The apparatus according to claim 1, wherein:
    said holding portion is shaped in the form of a pair of scissors, and the optical fiber is held by said holding portion so that the emitted laser light is incident upon a blade edge of the scissors.

12. The apparatus according to claim 1, wherein:
    said holding are on is shaped in the form of a pair of cooperating scissors elements each having a blade edge, and two optical fibers are provided and held by the cooperating scissors elements so that laser energy emitted from each of the two optical fibers is incident upon a respective blade edge of the other scissors cooperating element.

13. The apparatus according to claim 1, wherein:
    said holding portion has the form of tweezers having two arms and two optical fibers are respectively held on said holding portions so that the emitted laser energy from each of the two optical fibers is incident upon a pressure contact surface of each of the front end of two arms of the holding portion.

14. The apparatus according to claim 1, wherein:
    a radio frequency oscillator is connected to the blade so that the blade can be used as an electric knife.

* * * * *